(12) United States Patent
Madden et al.

(10) Patent No.: US 7,244,448 B2
(45) Date of Patent: Jul. 17, 2007

(54) LIPOSOMAL ANTINEOPLASTIC DRUGS AND USES THEREOF

(75) Inventors: Thomas D. Madden, Vancouver (CA); Sean C. Semple, Vancouver (CA); Quet F. Ahkong, Surrey (CA)

(73) Assignee: Tekmira Pharmaceuticals Corporation, Burnaby (CA)

( * ) Notice: Subject to any disclaimer, the term of this patent is extended or adjusted under 35 U.S.C. 154(b) by 0 days.

(21) Appl. No.: 09/896,812

(22) Filed: Jun. 29, 2001

(65) Prior Publication Data

US 2002/0110586 A1 Aug. 15, 2002

Related U.S. Application Data

(60) Provisional application No. 60/264,616, filed on Jan. 26, 2001, provisional application No. 60/215,556, filed on Jun. 30, 2000.

(51) Int. Cl.
*A61K 9/127* (2006.01)
(52) U.S. Cl. .................................... 424/450
(58) Field of Classification Search ............. 424/450; 264/4.1, 4.3
See application file for complete search history.

(56) References Cited

U.S. PATENT DOCUMENTS

| | | | |
|---|---|---|---|
| 5,023,087 A | 6/1991 | Yau-Young | |
| 5,543,152 A * | 8/1996 | Webb et al. | 424/450 |
| 5,552,156 A | 9/1996 | Burke | |
| 5,741,516 A | 4/1998 | Webb et al. | 424/450 |
| 5,837,282 A | 11/1998 | Fenske et al. | |
| 6,110,491 A * | 8/2000 | Kirpotin | |
| 6,355,268 B1 * | 3/2002 | Slater | |

FOREIGN PATENT DOCUMENTS

| | | |
|---|---|---|
| WO | WO 95/08986 A1 | 4/1995 |
| WO | WO 98/17256 A1 | 4/1998 |
| WO | 99/13816 * | 3/1999 |
| WO | WO 99/51202 A2 | 10/1999 |
| WO | WO 00/23052 A1 | 4/2000 |

OTHER PUBLICATIONS

Burris III et al., "Activity of topotecan, a new topoisomerase I inhibitor, against human tumor colony-forming units in vitro," *Journal of the National Cancer Institute* 84(23):1816-1820 (1992).
Clements et al., "Antiangiogenic potential of camptothecin and topotecan," *Cancer Chemother. Pharmacol.* 44:411-416 (1999).
Emerson et al., "In vivo antitumor activity of two new seven-substituted water-soluble camtothecin analogues," *Cancer Research* 55:603-609 (1995).

(Continued)

*Primary Examiner*—Gollamudi S. Kishore
(74) *Attorney, Agent, or Firm*—Seed IP Law Group PLLC

(57) ABSTRACT

This invention relates to liposomal antineoplastic agents (e.g., camptothecin) compositions and methods of using such compositions for treating neoplasia and for inhibiting angiogenesis. The compositions and methods are useful for modulating the plasma circulation half-life of an active agent.

5 Claims, 7 Drawing Sheets

OTHER PUBLICATIONS

Erickson-Miller et al., "Differential toxicity of camptothecin, topotecan and 9-aminocamptothecin to human, canine, and murine myeloid progenitors (CFU-GM) in vitro," *Cancer Chemother. Pharmacol.* 39:467-472 (1997).

Grochow et al., "Pharmacokinetics and pharmacodymanics of topotecan in patients with advanced cancer," *Drug Metabolism and Disposition* 20(5):706-713 (1992).

Hardman et al., "Efficacy of treatment of colon, lung and breast human carcinoma xenografts with: Doxorubicin, cisplatin, irinotecan or topotecan," *Anticancer Research* 19:2269-2274 (1999).

Hsiang et al., "Identification of mammalian DNA topoisomerase I as an intracellular target of the anticancer drug camptothecin," *Cancer Research* 48:1722-1726 (1988).

Madden et al., "The accumulation of drugs within large unilamellar vesicles exhibiting a proton gradient; a survey," *Chemistry and Physics of Lipids* 53:37-46 (1990).

Madden et al., "Encapsulation of topotecan in lipid-based carrier systems. Evaluation of drug stability and plasma elimination in a murine model, and comparison of antitumor efficacy against murine L 1210 and B16 tumors," *Proc. of ASCO*, 17:abstract #754 (1998).

Mayer et al., "Characterization of liposomal systems containing doxorubicin entrapped in response to pH gradients," *Biochimica et Biophysica Acta* 1025:143-151 (1990).

McCabe et al., "Comparative activity of oral and parenteral topotecan in murine tumor models: Efficacy of oral topotecan," *Cancer Investigation* 12(3):308-313 (1994).

O'Leary et al., "Antiangiogenic effects of camptothecin analogues 9-amino-20(S)-camptothecin, topotecan, and CPT-11 studied in the mouse cornea model," *Clinical Cancer Research* 5:181-187 (1999).

Ormrod and Spencer, "Topotecan: A review of its efficacy in small cell lung cancer," *Drugs* 58(3):533-551 (1999).

Tardi et al., "Liposomal encapsulation of topotecan enhances anticancer efficacy in murine and human xenograft models," *Cancer Research* 60:3389-3393 (2000).

Thompson et al., "Animal models for studying the action of topoisomerase I targeted drugs," *Biochimica et Biophysica Acta* 1400:301-319 (1998).

Wall et al., "Plant antitumor agents. I. The isolation and structure of camptothecin, a novel alkaloidal leukemia and tumor inhibitor from *Camptotheca acuminate*," *Journal of the American Chemical Society* 88(16):3888-3890 (1966).

\* cited by examiner

PK/Payout of Ionophore loaded Vinorelbine [Vinca 03]

Vinorelbine Retention in Blood

Lipid (ESM/CH) Recovery in Blood

Vinorelbine Recovery in Blood

PK/Payout of Ionophore loaded Vinorelbine [Vinca 03]

Vinorelbine Retention in Plasma

Lipid (ESM/CH) Recovery in Plasma

Vinorelbine Recovery in Plasma

PK/Payout of Ionophore loaded Vinblastine [Vinca 04]

Vinblastine Retention in Blood

Lipid (ESM/CH) Recovery in Blood

Vinblastine Recovery in Blood

PK/Payout of Ionophore loaded Vinblastine [Vinca 04]

Vinblastine Retention in Plasma

Lipid (ESM/CH) Recovery in Plasma

Vinblastine Recovery in Plasma

PK/Payout of Ionophore loaded Vinblastine [Vinca 04]

Vinblastine Retention in Blood

Lipid (ESM/CH) Recovery in Blood

Vinblastine Recovery in Blood

PK/Payout of Ionophore loaded Vinblastine [Vinca 04]

Vinblastine Retention in Plasma

Lipid (ESM/CH) Recovery in Plasma

Vinblastine Recovery in Plasma

PK/Payout of Ionophore loaded Topotecan

LIPOSOMAL ANTINEOPLASTIC DRUGS AND USES THEREOF

CROSS REFERENCE TO RELATED APPLICATIONS

This application is related to U.S. Provisional Application No. 60/215,556, filed Jun. 30, 2000, entitled "Liposomal Camptothecins and Uses Thereof," and U.S. Provisional Application No. 60/264,616, filed Jan. 26, 2001, entitled "Liposomal Antineoplastic Drugs and Uses Thereof," both of which are incorporated herein by reference in their entireties for all purposes. U.S. patent application Ser. No. 09/896,811, filed Jun. 29, 2001, entitled "Liposomal Camptothecins and Uses Thereof," is hereby incorporated by reference for all purposes.

BACKGROUND OF THE INVENTION

This invention relates to liposomal compositions and methods of using such compositions for treating neoplasia and for inhibiting angiogenesis.

Many anticancer or antineoplastic drugs have been encapsulated in liposomes. These include alkylating agents, nitrosouras, cisplatin, antimetabolites, and anthracyclines. Studies with liposomes containing anthracycline antibiotics have clearly shown reduction of cardiotoxicity and dermal toxicity and prolonged survival of tumor bearing animals compared to controls receiving free drug.

Liposomal anticancer drugs modify drug pharmacokinetics as compared to their free drug counterpart. For a liposomal drug formulation, drug pharmacokinetics will be largely determined by the rate at which the carrier is cleared from the blood and the rate at which the drug is released from the carrier. Considerable efforts have been made to identify liposomal carrier compositions that show slow clearance from the blood and long-circulating carriers have been described in numerous scientific publications and patents. Efforts have also been made to control drug leakage rates from liposomal carriers, using for example, transmembrane potential to control release.

Therapeutic camptothecins, such as Topotecan (9-dimethylaminomethyl-10-hydroxy-camptothecin; Hycamtin™), and Irinotecan, are a semi-synthetic, water soluble derivative of camptothecin, an alkaloid extracted from the stem wood of the Chinese tree *Camptotheca acuminata* (Wall, et al., *J. Am. Chem. Soc.* 88:3888-3890 (1966)). Camptothecins belong to the topoisomerase inhibitor class of antineoplastic agents, specifically inhibiting the action of the nuclear enzyme topoisomerase I which is involved in DNA replication (Hsiang, et al., *Cancer Res.* 48:1722-1726 (1988)). As such, topotecan exhibits a cell cycle-specific mechanism of action, acting during S-phase (DNA replication) to cause irreversible double strand breaks in DNA that ultimately lead to G2 cell cycle arrest and apoptosis. In the free form, the drug has a broad spectrum of activity against a range of tumor cell lines and murine allograft and human xenograft tumor models (McCabe, F. L. et al., *Cancer Invest* 12:308-313 (1994); Emerson, et al., *Cancer Res.* 55:603-609 (1995); Thompson, *Biochim. Biophys. Acta* 1400:301-319 (1998); Ormrod, et al., *Drugs* 58:533-551 (1999); Hardman, et al., *Anticancer Res.* 19:2269-2274 (1999)). More recently, evidence has emerged that topotecan has strong anti-angiogenic properties that may contribute to its anti-tumor mechanism of action (O'Leary, et al., *Clin. Cancer Res.* 5:181-187 (1999); Clements, et al., *Cancer Chemother. Pharmacol.* 44:411-416 (1999)). All these treatments are associated with dose-limiting toxicity such as non-cumulative myelosuppression leading to anaemia, neutropenia and thrombocytopenia, and gastrointestinal-related toxicity, including mucositis and diarrhea. Clinically, topotecan has been approved for second-line therapy in ovarian and small cell lung cancer (SCLC) and is currently the focus of extensive clinical evaluation.

Lipid formulations of camptothecins have been proposed as therapeutic agents (see, U.S. Pat. No. 5,552,156 and PCT Publication No. WO 95/08986. However, not all lipid formulations are equal for drug delivery purposes and extensive research continues into formulations which demonstrate preferred characteristics for drug loading and storage, drug administration, pharmacokinetics, biodistribution, leakage rates, tumor accumulation, toxicity profile, and the like. With camptothecins, the field is further complicated because dose limiting toxicities in humans may be 10-fold lower than in mice (Erickson-Miller, et al., *Cancer Chemother. Pharmacol.* 39:467-472 (1997)).

Improved liposomal formulations of antineoplastic agents could prove very useful. It is an object of the instant invention to provide lipid formulated antineoplastic agents having novel clinical utility.

SUMMARY OF THE INVENTION

The present invention provides compositions and methods useful for modulating the plasma circulation half-life of an active agent (e.g., topotecan). The liposomal formulations have increased clinical efficacy and decreased collateral toxicity. In addition, the present invention provides methods and liposomal compositions for treating neoplasia and inhibiting angiogenesis.

As such, in one embodiment, the present invention provides a method for modulating the plasma circulation half-life of an active agent, comprising: (a) providing a liposome having free active agent and precipitated active agent encapsulated therein; and (b) varying the amount of the active agent that is precipitated in the liposome. Surprisingly, by varying the amount of active agent that is precipitated in the liposome, it is possible to modulate the release kinetics of the active agent into the plasma. Preferred active agents are antineoplastic drugs, such as a camptothecin (e.g., topotecan).

In another embodiment, the present invention provides a liposomal formulation, comprising: a) an antineoplastic drug; and b) a liposome having free antineoplastic drug and precipitated antineoplastic drug, wherein the precipitated antineoplastic drug in the liposome is at least 50% of the total antineoplastic drug. By tailoring the amount of precipitated antineoplastic drug in the liposome, it is possible to control the release of the drug, both in vitro and in vivo. In certain preferred embodiments, high intraliposomal concentrations of the active agent (e.g., topotecan) results in a high amount of precipitated form. In this aspect, subsequent release rates of the drug in vivo are slow. In certain aspects, a slow release rate is preferable and more efficacious compared to a fast release rate.

In yet another embodiment, the present invention provides a liposomal formulation, comprising: a) an active agent; b) a liposome having free active agent and precipitated active agent encapsulated therein; and c) an empty liposome.

In this aspect, the serum half-life of the liposome is prolonged by including empty liposomes in the formulation. It will be readily apparent to those of skill in the art that any of a variety of lipids can be used to form the liposomal compositions of the present invention. In a presently preferred embodiment, the lipid comprises a mixture of sphingomyelin and cholesterol, preferably at a spingomyelin: cholesterol ratio (molar ratio) of about 30:70 to about 60:40. In one preferred embodiment, the liposome comprises sphingomyelin and cholesterol in a 55:45 ratio.

In still another aspect, the present invention provides a method of treating a solid tumor in a human afflicted therewith, the method comprising administering to the human an effective amount of a liposomal formulation of the present invention in a pharmaceutically acceptable carrier. A variety of solid tumors can be treated using the compositions of the present invention. In a preferred embodiment, the solid tumor to be treated is selected from the group consisting of solid tumors of the lung, mammary, colon and prostate. In another preferred embodiment, the method further comprises co-administration of a treatment or active agent suitable for treating neutropenia or platelet deficiency.

In a preferred embodiment, a liposomal topotecan is used to treat the solid tumors. In addition, it will be readily apparent to those of skill in the art that any of a variety of lipids can be used to form the liposomal compositions of the present invention.

Other features, objects and advantages of the invention and its preferred embodiments will become apparent from the detailed description which follows.

DETAILED DESCRIPTION OF THE INVENTION AND PREFERRED EMBODIMENTS

Figure 1A:
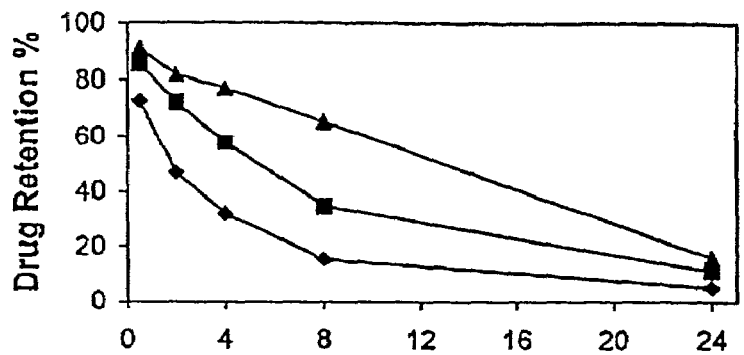
FIG. 1A-C shows the pharmacokinetic behavior of a liposomal formulation of vinorelbine. Panel A shows the rates of drug leakage from circulating carriers for three formulations of differing drug:lipid ratio (0.1:1, 0.2:1, 0.3:1). Drug release is dependent upon drug:lipid ratio with the slowest rate of release seen for the highest ratio (0.3:1). Panel B shows lipid recovery in the blood. Panel C shows that modulation in drug release rates from the carrier results in changes to the blood clearance half-life for vinorelbine.

The activity of many anticancer drugs is dependent on their pharmacokinetic behavior. This pharmacokinetic behavior defines the drug concentrations and period of time over which cancer cells are exposed to the drug. In the case of most anticancer drugs, longer exposure times are preferred as this results in increased killing of the cancer cells. In general, several parameters are used to describe drug pharmacokinetics. Plasma clearance half-time and area under the curve (AUC) are examples. The plasma clearance half-time is the time required for half of the administered drug to be removed from the plasma. The AUC is a measure of plasma drug levels over time and provides an indication of the total drug exposure. Generally, increased plasma clearance half-life and plasma AUC for an anticancer drug correlate with increased therapeutic efficacy.

I. Modulating Active Agent Release

The present invention describes methods and formulations for modulating drug release from liposomes. In one embodiment, the present invention provides a method for modulating the plasma circulation half-life of an active agent, comprising: (a) providing a liposome having free active agent and precipitated active agent encapsulated therein; and (b) varying the amount of the active agent that is precipitated in the liposome. Preferably, the "free active agent" and the "precipitate active agent" are the same active agent, however the present invention is not so limited. As used herein, the term "modulating" can mean either increasing or decreasing the release rate of the active agent from the liposomal carrier. For antineoplastic active agents, modulating is preferably decreasing or slowing the release rate of the active agent.

In preferred aspects, the liposomes of the present invention contain both encapsulated free active agent and precipitated active agent. The amount of active agent that is precipitated within the liposome can be varied using a variety of mechanisms. For example, by varying the active agent to lipid ratio the amount of active agent that is precipitated can be increased or decreased. Drug loading at low drug:lipid ratios, results in low concentrations of active agent (e.g., topotecan) in the liposome interior and hence most, if not all of the entire drug is in solution i.e., not precipitated or free. Low precipitation amounts result in a fast release rate of the drug from the liposome. Conversely, a high drug:lipid ratio results in high intraliposomal concentrations and high precipitation amounts. When the drug is in a precipitated form, subsequent release rates in vivo or in vitro are slow. For antineoplastic drugs (e.g., topotecan), slow release rates are preferable.

Without being bound by any particular theory, it is believed that the liposomes of the present invention undergo a "precipitation-dissolution mechanism" (PDM), which dictates drug release. In the PDM mechanism of the present invention, the dissolution rate of precipitated active agent (e.g., topotecan) within the lipsomome's interior into the internal solution of the liposome is slow, compared to the rate of release of active agent out of the liposome to the exterior and is thus rate determining. That is, the rate of dissolution of the precipitated drug to free drug in the liposome's interior determines how fast the drug will be released into the plasma.

In certain embodiments, the active agent to lipid ratio can be varied by the addition of empty liposomes. In general, liposomes whether empty or those having active agents contained therein are cleared by cells of the reticuloendothelial system (RES). Typically, the RES will remove 80-95% of a dose of injected liposomes within one hour, effectively out-competing the selected target site for uptake of the liposomes. A variety of factors which influence the rate of RES uptake of liposomes have been reported including, liposome size, charge, degree of lipid saturation, and surface moieties. By including empty liposome vesicles, it is possible to shield the liposomes containing active agent from the RES. Thus, empty liposome vesicles actually extend the blood circulation lifetime of the liposomes by acting as "decoys". An extended circulation time is often needed for liposomes to reach the target region, cell or site from the site of injection. The empty liposomal vesicles keep the RES busy and as a result, the serum half-life of the liposomes having active agent contained therein is increased.

In certain other aspects, a component(s) is added to the liposome that will enhance the precipitation of the active agent. In this aspect, a variety of charged ions can be used to increase the amount of precipitated active agent in the vesicle's interior. In preferred aspects, divalent, trivalent or polyvalent anions are used. Suitable anions include, but are not limited to, carboxylate ($—CO_2^-$), sulfonate ($SO_3^-$), sulfate ($SO_4^{-2}$), hydroxide (—OH), alkoxides, phosphate ($—PO_4^{-2}$), and phosphonate ($—PO_3^{-2}$). Those of skill in the art will know of other components, which will enhance the amount of precipitated active agent in the liposome's interior.

Moreover, the drug:lipid ratios can be varied using the size of the liposome. The larger the liposome vesicle used, the smaller the drug:lipid ratio. In certain aspects, both the active agent to lipid ratio and the size of the liposome are varied to optimize the efficacy of the active agent.

The amount of encapsulated active agent that is precipitated in vesicle will vary and is somewhat dependent on the active agent itself. In certain embodiments, the amount of precipitated active agent is at least about 25% to about 95% (such as about 25%, 30%, 35%, 40%, 45%, 50%, 55%, 60%, 65%, 70%, 75%, 80%, 85%, 90% and 95%) of total active agent. For topotecan, the amount of the precipitated active agent encapsulated in the liposome is at least 50% of the total active agent.

In preferred aspects, when the active agent is an antineoplastic drug, using higher drug:lipid ratios results in higher amounts of encapsulated precipitated drug. As a result, drug release from the liposomes in vivo is slower than for similar compositions prepared at lower drug:lipid ratio. These higher drug:lipid ratio liposomes exhibit extended plasma half-life and increased plasma AUC values. Advantageously, these formulations exhibit improved antitumor efficacy.

In certain embodiments, the ratio of active agent:lipid is about 0.005-1:1 (w/w).

Preferably, the ratio of active agent:lipid is about 0.05-0.9:1 (w/w) and more preferably, the ratio of active agent:lipid is about 0.1-0.5:1 (w/w). By modulating the plasma circulation half-life of the active agent, it is thus possible to maximize or optimize efficacy of the active agent.

II. Compositions and Methods of Making Liposomal Formulations

Liposome, vesicle and liposome vesicle will be understood to indicate structures having lipid-containing membranes enclosing an aqueous interior. The structures can have one or more lipid membranes unless otherwise indicated, although generally the liposomes will have only one membrane. Such single-layered liposomes are referred to herein as "unilamellar." Multilayer liposomes are referred to herein as "multilamellar."

The liposomes that are used in the present invention are preferably formed from lipids which when combined form relatively stable vesicles. An enormous variety of lipids are known in the art, which can be used to generate such liposomes. Preferred lipids include, but are not limited to, neutral and negatively charged phospholipids or sphingolipids and sterols, such as cholesterol. The selection of lipids is generally guided by consideration of, e.g., liposome size and stability of the liposomes in the bloodstream.

Preferred liposome compositions for use in the present invention include those comprising sphingomyelin and cholesterol. The ratio of sphingomyelin to cholesterol in the liposome composition can vary, but generally is in the range of from about 75/25 mol %/mol % sphingomyelin/cholesterol to about 30/50 mol %/mol % sphingomyelin/cholesterol, more preferably about 70/30 mol %/mol % sphingomyelin/cholesterol to about 40/45 mol %/mol % sphingomyelin/cholesterol, and even more preferably about 55/45 mol %/mol % sphingomyelin/cholesterol. Other lipids can be included in the liposome compositions of the present invention as may be necessary, such as to prevent lipid oxidation or to attach ligands onto the liposome surface. Generally, if lipids are included, the other inclusion of such lipids will result in a decrease in the sphingomyelin/cholesterol ratio. Liposomes of this type are known as sphingosomes and are more fully described in U.S. Pat. No. 5,814,335, the teachings of which are incorporated herein by reference.

A variety of methods are available for preparing liposomes as described in, e.g., Szoka, et al., *Ann. Rev. Biophys. Bioeng.* 9:467 (1980); U.S. Pat. Nos. 4,235,871; 4,501,728; 4,837,028, the text Liposomes, Marc J. Ostro, ed., Marcel Dekker, Inc., New York, 1983, Chapter 1; and Hope, et al, *Chem. Phys. Lip.* 40:89 (1986), all of which are incorporated herein by reference. The protocol for generating liposomes generally includes: mixing of lipid components in an organic solvent; drying and reconstituting liposomes in aqueous solvent; and sizing of liposomes (such as by extrusion), all of which are well known in the art.

Alternative methods of preparing liposomes are also available. For instance, a method involving detergent dialysis based self-assembly of lipid particles is disclosed and claimed in U.S. Pat. No. 5,976,567 issued to Wheeler, et al., which avoids the time-consuming and difficult to-scale drying and reconstitution steps. Further methods of preparing liposomes using continuous flow hydration are under development and can often provide the most effective large scale manufacturing process.

Preparation of liposomal formulations having active agents (e.g., camptothecins) requires loading of the drug into the liposomes. Loading can be either passive or active. Passive loading generally requires addition of the drug to the buffer at the time of the reconstitution step. This allows the drug to be trapped within the liposome interior, where it will remain if it is not lipid soluble, and if the vesicle remains intact (such methods are employed, for example, in PCT Publication No. WO 95/08986, the teachings of which are incorporated herein by reference).

Active loading is in many ways preferable, and a wide variety of therapeutic agents can be loaded into liposomes with encapsulation efficiencies approaching 100% by using a transmembrane pH or ion gradient (see, Mayer, et al., *Biochim. Biophys. Acta* 1025:143-151 (1990) and Madden, et al., *Chem. Phys. Lipids* 53:37-46 (1990)). Numerous ways of active loading are known to those of skill in the art. All such methods involve the establishment of some form of gradient that draws lipophilic compounds into the interior of liposomes where they can reside for as long as the gradient is maintained. Very high quantities of the desired drug can be obtained in the interior, so much that the drug may precipitate out on the interior and generate a continuing uptake gradient.

Particularly preferred for use with the instant invention is ionophore-mediated loading as disclosed and claimed in U.S. Pat. No. 5,837,282, the teachings of which are incorporated by reference herein. The ionophore-mediated loading is an electroneutral process and does not result in formation of a transmembrane potential. With hydrogen ion transport into the vesicle there is concomitant magnesium ion transport out of the vesicle in a 2:1 ratio (i.e. no net charge transfer). In the case of topotecan, it is thought that the agent crosses the membrane in a neutral state (no charge). Upon entry into the vesicle, topotecan becomes positively charged. As ionophore-mediated loading is an electroneutral process, there is no transmembrane potential generated.

An important characteristic of liposomal camptothecins for pharmaceutical purposes is the drug to lipid ratio of the final formulation. As discussed earlier, drug:lipid ratios can be established in two ways: 1) using homogenous liposomes each containing the same drug:lipid ratio; or 2) by mixing empty liposomes with liposomes having a high drug:lipid ratio to provide a suitable average drug:lipid ratio. For different applications, different drug:lipid ratios may be desired. Techniques for generating specific drug:lipid ratios are well known in the art. Drug:lipid ratios can be measured on a weight to weight basis, a mole to mole basis or any other designated basis. Preferred drug:lipid ratios range from about 0.005:1 drug:lipid (by weight) to about 0.2:1 drug:lipid (by weight) and, more preferably, from about 0.1:1 drug:lipid (by weight) to about 0.3:1 drug:lipid (by weight).

A further important characteristic is the size of the liposome particles. For use in the present inventions, liposomes having a size of from about 0.05 microns to about 0.15 microns are preferred.

The present invention also provides liposomal compositions (e.g., camptothecin) in kit form. The kit can comprise a ready-made formulation, or a formulation, which requires mixing of the medicament before administration. The kit will typically comprise a container that is compartmentalized for holding the various elements of the kit. The kit will contain the liposomal compositions of the present invention or the components thereof, possibly in dehydrated form, with instructions for their rehydration and administration.

The liposome compositions prepared, for example, by the methods described herein can be administered either alone or in a mixture with a physiologically acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the composition may include lipid-protective agents, which protect lipids against free-radical and lipid-peroxidative damages on storage. Lipophilic free-radical quenchers, such as $\alpha$.-tocopherol and water-soluble iron-specific chelators, such as ferrioxamine, are suitable.

A wide variety of active agents are suitable for the liposomal compositions and methods of the present invention. In a preferred aspect, the active agents are antineoplastic drugs. Currently, there are approximately twenty recognized classes of approved antineoplastic drugs. The classifications are generalizations based on either a common structure shared by particular drugs, or are based on a common mechanism of action by the drugs. A partial listing of some of the commonly known commercially approved (or in active development) antineoplastic agents by classification is as follows:

Structure-Based Classes:

1. Fluoropyrimidines—5-FU, Fluorodeoxyuridine, Ftorafur, 5'-deoxyfluorouridine, UFT, S-1 Capecitabine;

2. Pyrimidine Nucleosides—Deoxycytidine, Cytosine Arabinoside, 5-Azacytosine, Gemcitabine, 5-Azacytosine-Arabinoside;

3. Purines—6-Mercaptopurine, Thioguanine, Azathioprine, Allopurinol, Cladribine, Fludarabine, Pentostatin, 2-Chloro Adenosine;

4. Platinum Analogues—Cisplatin, Carboplatin, Oxaliplatin, Tetraplatin, Platinum-DACH, Ormaplatin, CI-973, JM-216;

5. Anthracyclines/Anthracenediones—Doxorubicin, Daunorubicin, Epirubicin, Idarubicin, Mitoxantrone;

6. Epipodophyllotoxins—Etoposide, Teniposide;

7. Camptothecins—Irinotecan, Topotecan, 9-Amino Camptothecin, 10,11-Methylenedioxy Camptothecin, 9-Nitro Camptothecin, TAS 103, 7-(4-methyl-piperazino-methylene)-10, 11-ethylenedioxy-20(S)-camptothecin, 7-(2-N-isopropylamino)ethyl)-20(S)-camptothecin;

8. Hormones and Hormonal Analogues—Diethylstilbestrol, Tamoxifen, Toremefine, Tolmudex, Thymitaq, Flutamide, Bicalutamide, Finasteride, Estradiol, Trioxifene, Droloxifene, Medroxyprogesterone Acetate, Megesterol Acetate, Aminoglutethimide, Testolactone and others;

9. Enzymes, Proteins and Antibodies—Asparaginase, Interleukins, Interferons, Leuprolide, Pegaspargase, and others;

10. Vinca Alkaloids—Vincristine, Vinblastine, Vinorelbine, Vindesine;

11. Taxanes—Paclitaxel, Docetaxel.

Mechanism-Based Classes:

1. Antihormonals—See classification for Hormones and Hormonal Analogues, Anastrozole;

2. Antifolates—Methotrexate, Aminopterin, Trimetrexate, Trimethoprim, Pyrrexim, Pyrimethamine, Edatrexate, MDAM;

3. Antimicrotubule Agents—Taxanes and Vinca Alkaloids;

4. Alkylating Agents (Classical and Non-Classical)—Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, Dacarbazine and others;

5. Antimetabolites—Purines, pyrimidines and nucleosides, listed above;

6. Antibiotics—Anthracyclines/Anthracenediones, Bleomycin, Dactinomycin, Mitomycin, Plicamycin, Pentostatin, Streptozocin;

7. Topoisomerase Inhibitors—Camptothecins (Topo I), Epipodophyllotoxins, m-AMSA, Ellipticines (Topo II);

8. Antivirals—AZT, Zalcitabine, Gemcitabine, Didanosine, and others;

9. Miscellaneous Cytotoxic Agents—Hydroxyurea, Mitotane, Fusion Toxins, PZA, Bryostatin, Retinoids, Butyric Acid and derivatives, Pentosan, Fumagillin, and others.

The objective of all antineoplastic drugs is to eliminate (cure) or to retard the growth and spread (remission) of the cancer cells. The majority of the above listed antineoplastic agents pursue this objective by possessing primary cytotoxic activity, effecting a direct kill on the cancer cells. Other antineoplastic drugs stimulate the body's natural immunity to effect cancer cell kill. The literature is replete with discussions on the activity and mechanisms of all of the above drugs, and many others.

Exemplary methods of making specific formulations of liposomal camptothecins and, in particular, liposomal topotecan are set out in the examples below.

III. Methods of Using Liposomal Camptothecins

The liposomal compositions (e.g., camptothecins) of the present invention are used, in the treatment of solid tumors in an animal, such as a human. The examples below set out key parameters of the drug:lipid ratios, dosages of active agent and lipid to be administered, and preferred dose scheduling to treat different tumor types.

Preferably, the pharmaceutical compositions are administered parenterally, i.e., intraarticularly, intravenously, intraperitoneally, subcutaneously or intramuscularly. More preferably, the pharmaceutical compositions are administered by intravenous drip or intraperitoneally by a bolus injection. The concentration of liposomes in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration can be increased to lower the fluid load associated with treatment. Alternatively, liposomes composed of irritating lipids can be diluted to low concentrations to lessen inflammation at the site of administration. The amount of liposomes administered will depend upon the particular camptothecin used, the disease state being treated and the judgement of the clinician, but will generally, in a human, be between about 0.01 and about 50 mg per kilogram of body weight, preferably between about 5 and about 40 mg/kg of body weight. Higher lipid doses are suitable for mice, for example, 50-120 mg/kg.

Dosage for the active agent (e.g., camptothecin) will depend on the administrating physician's opinion based on age, weight, and condition of the patient, and the treatment schedule. A recommended dose for free topotecan in Small Cell Lung Cancer is 1.5 mg/M$^2$ per dose, every day for 5 days, repeated every three weeks. Because of the improvements in treatment now demonstrated in the examples, below, doses of active agent (e.g., topotecan) in humans will be effective at ranges as low as from 0.015 mg/M$^2$/dose and will still be tolerable at doses as high as 15 to 75 mg/M$^2$/dose, depending on dose scheduling. Doses may be single doses or they may be administered repeatedly every 4 h, 6 h, or 12 h or every 1 d, 2 d, 3 d, 4 d, 5 d, 6 d, 7 d, 8 d, 9 d, 10 d or combination thereof. Preferred scheduling may employ a cycle of treatment that is repeated every week, 2 weeks, three weeks, four weeks, five weeks or six weeks or combination thereof. In a presently preferred embodiment, treatment is given once a week, with the dose typically being less than 1.5 mg/M$^2$.

Particularly preferred topotecan dosages and scheduling are as follows:

| Dosage (mg/M$^2$/dose) | Period | Repeat Cycle every: |
|---|---|---|
| 0.15 | 1 d × 5 d | 3 weeks |
| 0.5 | 1 d | 1 week |
| 1.5 | 1 d | 1 week |
| 15 | 1 d | 3 weeks |
| 50 | 1 d | 3 weeks |

The invention will be described in greater detail by way of specific examples. The following examples are offered for illustrative purposes, and are not intended to limit the invention in any manner. Those of skill in the art will readily recognize a variety of non-critical parameters, which can be changed or modified to yield essentially the same results.

IV. EXAMPLES

A. Materials and Methods

1. Materials. Topotecan (Hycamtin™, SmithKline Beecham) was purchased from the pharmacy at the British Columbia Cancer Agency. Sphingomyelin (SM) was purchased from Avanti Polar Lipids. Sphingomyelin from Northern Lipids was used in an early study, but was less soluble in ethanol than the Avanti version. Cholesterol (CH) and the divalent cation ionophore A23187 were purchased from Sigma. [$^3$H]-cholesterylhexadecylether (Dupont) was used as a lipid marker.

2. Mice. Female, ICR, BDF-1 or athymic nu/nu (6-8 weeks) were purchased from Harlan-Sprague Dawley (Indianapolis, Ind.). All animals were quarantined for one week prior to use. All studies were conducted in accordance with the guidelines established by the Canadian Council on Animal Care (CCAC) and the Institutional Animal Care and User Committee (IACUC).

3. Formulation of topotecan by the Mg-A23187 method. Topotecan was encapsulated in SM:CH (55:45, mol/mol) liposomes using the Mg-A23187 ionophore method according to U.S. Pat. No. 5,837,282. The initial drug-to-lipid ratio was 0.10 (w/w) and drug loading was typically 95-100%. The external buffer consisted of 10 mM PBS, pH 7.5 and 300 mM sucrose. All formulations were analyzed with respect to particle size, drug loading efficiency, pH, and drug and lipid concentration.

4. Drug preparation and dosing. Each vial of topotecan (Hycamtin™) was hydrated in 1.0 ml of sterile water, giving a topotecan concentration of 4.0 mg/ml. Subsequent dilutions were μl made in 0.9% sterile saline to maintain the low pH required for the lactone species of the drug. Unused drug in the water stock solution (4.0 mg/ml) was stored at 4° C. in the absence of light. Liposome encapsulated topotecan was diluted in 0.9% saline to the required concentration for administration. All drug administrations were at 10 ml/kg (200 μl/20 g mouse) via the lateral tail vein.

5. Pharmacokinetic and in vivo leakage studies. The pharmacokinetics and drug leakage of free and liposome encapsulated topotecan were evaluated in ICR mice over 24 h following i.v. administration via the lateral tail vein. Two different drug-to-lipid ratios, i.e., 0.10 (w/w) and 0.02 (w/w), were used to examine the influence of drug-to-lipid ratio and lipid dose on drug leakage and PK behavior. Encapsulated topotecan was administered at 1 mg/kg (10 or 50 mg/kg lipid) and 5 mg/kg topotecan (50 mg/kg lipid). Correspondingly, the PK behavior of free topotecan was evaluated at and 1 and 5 mg/kg. Total topotecan in blood was determined by a fluorescence assay preceded by precipitation of plasma proteins. Topotecan was quantified by spectrofluorimetry at an excitation (2.5 nm slit width) and emission wavelength (2.5 nm slit width) of 380 and 518 nm, respectively. Lipid levels in plasma were determined by liquid scintillation counting of the [$^3$H]-CHE label.

6. MTD studies. MTD studies were performed in the host mouse strain corresponding to each tumor model. Single dose and multidose MTD were determined by monitoring weight loss over time. The MTD was defined as the dose that resulted in 20% weight loss.

7. Myelosuppression and neutropenia studies. Alteration in peripheral blood cell levels as a consequence of topotecan administration was assessed over 4-6 weeks in ICR mice. Blood was collected into EDTA microtainer tubes at Day 1, 3, 5, 7, 14, and 21 following i.v. administration of free or liposome encapsulated topotecan at 10 mg/kg. Empty vesicles were administered as a control. CBC and differential analysis was performed at Central Labs for Veterinarians (Langley, BC) to quantify cellular levels, ratios and morphology.

8. Tumor Models. The L1210 murine leukemia model and the CT-26 murine colon metastases model were employed as in standard protocols. Human MX-1 and LX-1 cell lines were obtained from the DCTD Tumor Repository in Frederick, Md. These cell lines were received as tumor fragments and were propagated in NCr nude mice by serial transplantation of 3×3 mm fragments. Experiments were not initiated until the cell lines had been through 3 passages in nude mice and the tumor lines were restarted when the passage number reached 10.

9. Efficacy Studies. All dosing of free and liposomal topotecan was administered by the intravenous route at 10 ml/kg via the lateral tail vein. In the L1210 and CT-26 models, dosing occurred on day 1 (tumor cell injection=day 0). For the MX-1 and LX-1 tumor models, tumor volume was determined by repeated perpendicular measurements of tumor dimensions and using the formula:

Volume (mm$^3$)=$(L \times W^2)/2$

Dosing was initiated in the MX-1 and LX-1 models when tumors had clearly demonstrated growth and were in the range 100-300 mm$^3$.

Since most drugs exhibit a balance between a biological effect and toxicity, it is useful to examine a parameter that incorporates both of these attributes. The most commonly employed parameter is therapeutic index (TI). Traditionally, therapeutic index is defined as:

TI=$LD_{50}/ED_{50}$

However, since it is no longer permissible to perform LD50 studies, therapeutic index for these studies has been defined as follows:

TI=MTD/MED.

In the above formula, MTD is the maximum tolerated dose, defined as that dose that causes a mean weight loss of 20% in a group of animals; and MED is the minimal effective dose, defined as the dose that produces an optimal % T/C value of ≦40 in the solid tumor models or an % ILS of 50±10% in the survival models.

B. Results

Figure 1B:
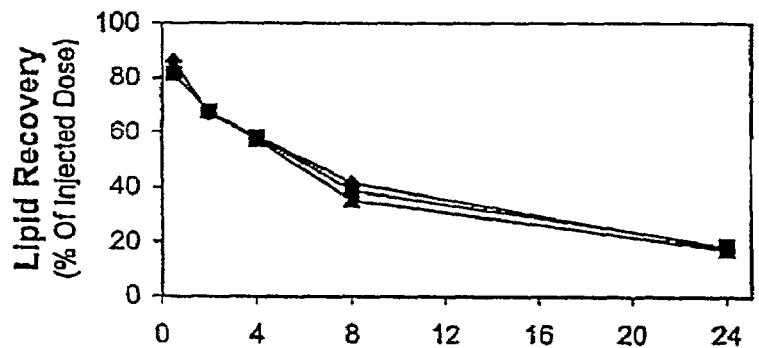
Figure 1C:
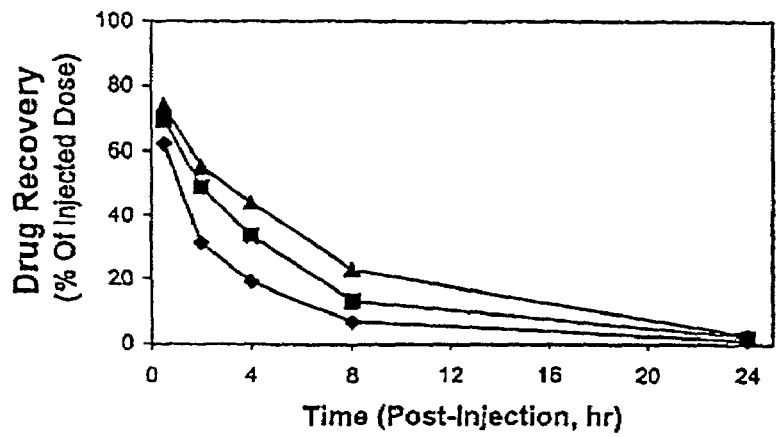

1. Pharmacokinetics and drug leakage. The influence of liposome encapsulation and drug-to-lipid ratio on plasma pharmacokinetics and drug leakage of topotecan was examined over 24 h in ICR mice. Liposome encapsulation of topotecan (drug-to-lipid ratio, 0.11, wt/wt) had a dramatic influence on the pharmacokinetics parameters of the drug (see, FIG. 1, top; and Table 1). At a 5 mg/kg dose of topotecan, a 164-fold increase in plasma AUC, a 24-fold increase in $C_{max}$ and a 24-fold increase in the plasma α half-life were observed for the liposomal drug relative to the free drug (see, Table 1). Historically, large improvements in AUC and plasma half-lives of liposomal drugs have resulted in enhanced delivery of the drug to disease-sites (such as tumors), a process known as "disease-site targeting".

The formulations used in this study were prepared by the Mg-A23187 ionophore method. There was an initial rapid release of drug in the first 10-30 minutes after iv administration (see, FIG. 1, bottom), followed by a more gradual release phase. The $t_{1/2}$ release for the Mn-A23187 and Mg-A23187 formulations were ~3 h and ~5-7 h, respectively; however, very little drug was present in either formulation at 24 h.

For most liposomal drug formulations, the pharmacokinetic properties of the encapsulated drug are controlled by the lipid composition and dose. Liposomal topotecan has been shown to exhibit exceptional anti-tumor activity, even at very low drug doses (0.5 mg/kg; drug-to-lipid ratio, 0.10, wt/wt). At these drug doses and drug-to-lipid ratio, liposome elimination from the plasma is expected to be rapid. Therefore, to determine whether the pharmacokinetics of topotecan at low doses could be improved, a low drug-to-lipid ratio (0.02, wt/wt) formulation of topotecan was investigated. Interestingly, in this study, the low drug-to-lipid ratio formulation released the drug much faster than the higher drug-to-lipid ratio (0.11, wt/wt) formulation. This result was unexpected.

TABLE 1

Pharmacokinetic parameters of free and liposomal topotecan.

| Formulation | Dose (mg/kg) | AUC (h · μg/ml) | Cmax (μg/ml) | Cl (ml/h) | α½ (h) | β½ (h) |
|---|---|---|---|---|---|---|
| Free | 1 | 1.97 | 0.75 | 13.9 | 0.14 | 11.8 |
|  | 5 | 2.77 | 2.17 | 49.6 | 0.26 | 11.4 |
| TCS | 1 | 65.7 | 16.3 | 0.417 | 2.79 |  |
|  | 5 | 453 | 51.0 | 0.302 | 6.16 |  |

All parameters were derived from one or two-compartment models using WINNONLIN PK modeling software.

Figure 2A:
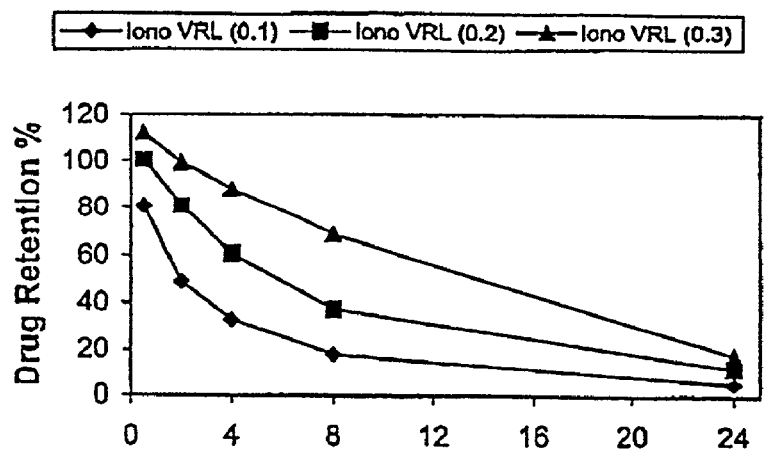
FIG. 2A-C shows a corresponding behavior when plasma drug levels are used to follow pharmacokinetics. Panel A shows drug retention versus time. Panel B shows lipid recovery versus time. Panel C shows drug recovery versus time.
Figure 2B:
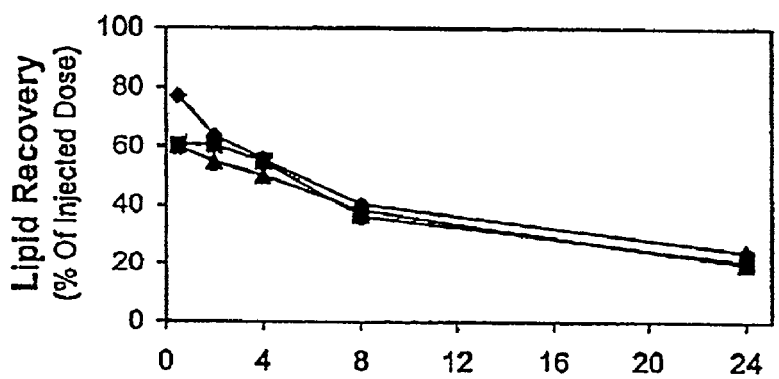
Figure 2C:
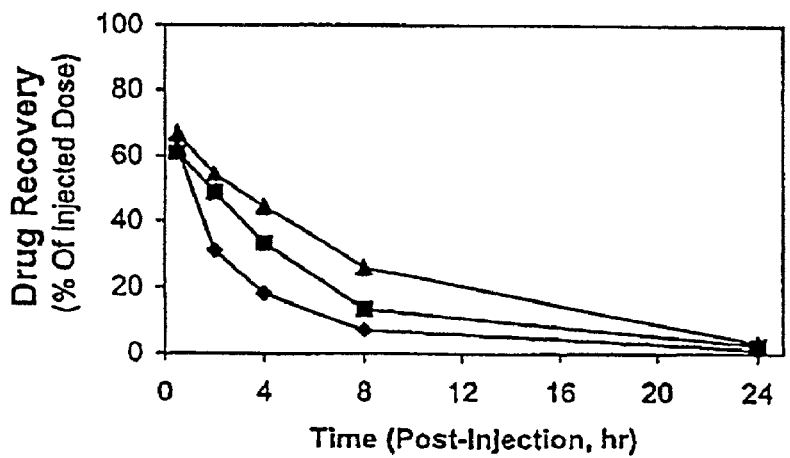

2. Maximum tolerated doses. Single and multidose MTD studies were performed in tumor bearing Balb/c, BDF-1 and NCr nu/nu mice. Body weights of individual mice were monitored throughout each study to evaluate the general tolerability of free and liposomal topotecan and, where possible, to establish an MTD (see, FIG. 2). The maximum tolerated dose of liposomal topotecan was 10 mg/kg on a single administration, 7.5 mg/kg on a q7dx3 schedule and 5 mg/kg on a q3dx4 schedule. The reported $LD_{10}$ of free topotecan following a single intravenous infusion in mice is 75 mg/M$^2$ (~25 mg/kg) [Hycamtin™ product monograph]; however, very little weight loss was observed at doses up to 40 mg/kg, although this was considered the MTD due to acute responses. Drug quantities were limited so doses higher than 40 mg/kg (administered over 5-10 minutes) were not pursued. It has previously been indicated that the $LD_{10}$ of free topotecan on a qdx5 schedule is 14 mg/M2/dose (~4.7 mg/kg/dose) (Grochow, , et al., *Drug Metab. Dispos.* 20:706-713 (1992)).

3. Toxicity. The major dose-limiting toxicity of free topotecan administered daily in humans for 5 consecutive days (dx5) at 1.5 mg $M^2$/dose, the MTD, is non-cumulative myelosuppression. As mentioned earlier, humans are more sensitive than mice to myelosuppression and can only tolerate 11% of the MTD in mice (1.5 vs 14 mg/$M^2$). In this regard, dogs have been shown to be a much better predictor of topotecan myelosuppression in humans (Burris, et al., *J. Natl. Cancer Inst.* 84:1816-1820 (1992)). However, mice should be suitable for comparing the relative myelosuppressive effects of free and liposome encapsulated topotecan.

phocyte sub-population were reduced approximately 2-fold for liposomal topotecan relative to control animals. No significant differences were observed in these parameters for free topotecan at the same dose. At day 21 post-injection total, WBC levels for liposomal topotecan remained approximately 2.5-fold lower than normal animals; however, neutrophils levels had recovered from a 20-fold decrease to a 3-fold decrease relative to normal mice. Lymphocyte levels remained ~2-fold lower than normal mice. No other significant differences were observed.

Analysis of serum chemistry parameters at day 3 post-injection revealed very few changes relative to untreated animals (see, Table 3). The only change of note was a statistically significant increase (~2-fold) in globulin levels and a concomitant decrease in the albumin/globulin ratio for animals treated with liposomal topotecan. No other significant changes were observed.

TABLE 2

Blood CBC and differential of ICR mice treated with a 10 mg/kg i.v. dose of free or liposome encapsulated topotecan.

| Treatment | Day Post-Injection | WBC ($\times 10^9$/L) | WBC Differential | | | | |
|---|---|---|---|---|---|---|---|
| | | | Neutro ($\times 10^9$/L) | Lympho ($\times 10^9$/L) | Mono ($\times 10^9$/L) | Eosino ($\times 10^9$/L) | Baso ($\times 10^9$/L) |
| Control | | 6.47 ± 1.62 | 0.937 ± 0.201 | 5.23 ± 1.45 | 0.180 ± 0.042 | 0.059 ± 0.039 | 0.056 ± 0.053 |
| Free | 3 | 6.70 ± 1.95 | 0.520 ± 0.200 | 5.90 ± 1.70 | 0.177 ± 0.072 | 0.031 ± 0.021 | 0.057 ± 0.040 |
| | 21 | 5.16 ± 1.18 | 0.480 ± 0.122 | 4.33 ± 0.93 | 0.247 ± 0.180 | 0.034 ± .016 | 0.088 ± 0.071 |
| TCS | 3 | 2.82 ± 1.05 | 0.048 ± 0.018 | 2.63 ± 0.87 | 0.109 ± 0.126 | 0.001 ± 0.001 | 0.034 ± 0.029 |
| | 21 | 2.54 ± 1.43 | 0.282 ± 0.167 | 2.06 ± 1.36 | 0.133 ± 0.142 | 0.019 ± 0.011 | 0.064 ± 0.060 |
| Empty | 3 | 4.68 ± 1.13 | 0.598 ± 0.238 | 3.66 ± 0.93 | 0.248 ± 0.168 | 0.081 ± 0.044 | 0.064 ± 0.055 |
| | 21 | 5.05 ± 0.64 | 0.898 ± 0.575 | 3.78 ± 0.88 | 0.263 ± 0.163 | 0.038 ± 0.036 | 0.072 ± 0.057 |

| Treatment | RBC ($\times 10^{12}$/L) | Hb (g/L) | Hc (L/L) | PLT ($\times 10^9$/L) |
|---|---|---|---|---|
| Control | 8.67 ± 0.93 | 142 ± 12 | 0.438 ± 0.045 | 717 ± 317 |
| Free | 8.47 ± 0.39 | 136 ± 05 | 0.444 ± 0.012 | 879 ± 145 |
| | 9.81 ± 0.37 | 154 ± 04 | 0.493 ± 0.014 | 907 ± 059 |
| TCS | 8.93 ± 0.76 | 141 ± 10 | 0.463 ± 0.033 | 564 ± 098 |
| | 9.41 ± 0.83 | 154 ± 12 | 0.486 ± 0.035 | 1009 ± 161 |
| Empty | 7.77 ± 0.30 | 130 ± 05 | 0.416 ± 0.014 | 863 ± 143 |
| | 9.36 ± 0.67 | 152 ± 08 | 0.483 ± 0.033 | 1366 ± 144 |

TABLE 3

Serum chemistry panel of ICR mice treated with a 10 mg/kg i.v. dose of free or liposome encapuslated topotecan-day 3 post-injection.

| Treatment | BUN (mmol/L) | Creatinine (μmol/L) | TP (g/L) | Albumin (g/L) | Globulin (g/L) | Alb/Glob Ratio | Bilirubin (μmol/L) | Alk Phos (IU/L) | ALT (IU/L) | AST (IU/L) | CPK (IU/L) |
|---|---|---|---|---|---|---|---|---|---|---|---|
| Control | 11.3 ± 3.0 | 83 ± 6 | 46.7 ± 2.1 | 31.3 ± 1.5 | 15.3 ± 1.2 | 2.07 ± 0.15 | 4.7 ± 0.6 | 86 ± 12 | 27 ± 31 | 59 ± 22 | 87 ± 107 |
| Free | 9.4 ± 3.2 | 82 ± 18 | 48.0 ± 2.1 | 32.8 ± 1.3 | 15.2 ± 1.1 | 2.16 ± 0.15 | 3.8 ± 0.8 | 67 ± 35 | 13 ± 23 | 55 ± 10 | 56 ± 38 |
| TCS | 10.0 ± 3.9 | 96 ± 28 | 55.8 ± 11.8 | 28.8 ± 2.5 | 27.0 ± 10.1 | 1.18 ± 0.33 | 2.5 ± 0.6 | 73 ± 21 | 23 ± 17 | 77 ± 29 | 155 ± 54 |
| Empty | ND | 68 ± 13 | 49.3 ± 1.2 | 33.0 ± 1.7 | 16.3 ± 0.6 | 2.00 ± 0.17 | 4.3 ± 0.6 | 70 ± 10 | 17 ± 15 | 53 ± 6 | 56 ± 26 |

In a study, the maximal reduction in peripheral WBC counts occurred at day 3 post-injection following administration of liposomal topotecan. A comparison of peripheral blood cell levels and morphology was then made at day 3 following administration of free or liposome encapsulated topotecan or empty vesicles (see, Table 2). The dose used for this comparison was the MTD of liposome-encapsulated topotecan (10 mg/kg). A significant reduction in circulating neutrophils was observed for liposomal topotecan relative to free topotecan (~10-fold), empty vesicles (~10-fold) or control animals (~20-fold). Total WBC levels and the lym- C. Efficacy Studies in Murine and Human Tumor Models: Single Dose Studies 1. L1210 Murine Leukemia. The intravenous L1210 murine leukemia model has been used extensively to evaluate differential activity between free and liposome encapsulated chemotherapeutic agents and was one of the original (1955-1975) models in the in vivo NCI screen of novel chemotherapeutic agents (Plowman, et al., *Human tumor xenograft models in NCI drug development. In "Anticancer Drug Development Guide: Preclinical Screening, Clinical Trials, and Approval"* (B. Teicher, Ed.), Humana Press Inc., Totowa (1997); Waud, *Murine L1210 and P388 leukemias. In "Anticancer Drug Development Guide: Preclinical Screening, Clinical Trials, and Approval"* (B. Teicher, Ed.), Humana Press Inc., Totowa (1997)). The model is rapid— the mean survival of untreated animals is typically~7-8 days—and the administered tumor cells seed in the liver and bone marrow.

Figure 3A:
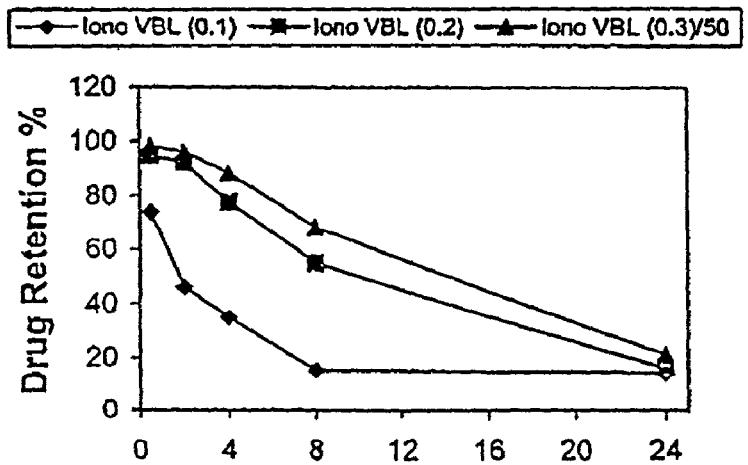
FIG. 3A-C shows the pharmacokinetic behavior of formulations of liposomal vinblastine as a function of drug: lipid ratio (blood PK). Drug leakage from the liposomal carrier is determined by the initial drug:lipid ratio with slower release for formulations of higher drug ratio. Panel A shows drug retention versus time. Panel B shows lipid recovery versus time. Panel C shows drug release rates correlate with changes to drug clearance half-life from the blood.
Figure 3B:
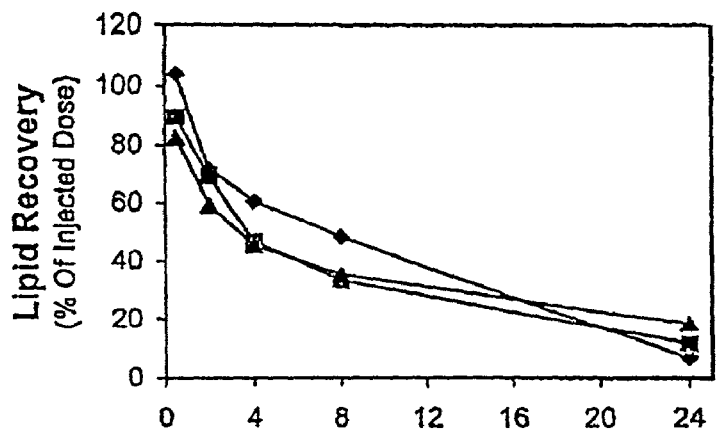
Figure 3C:
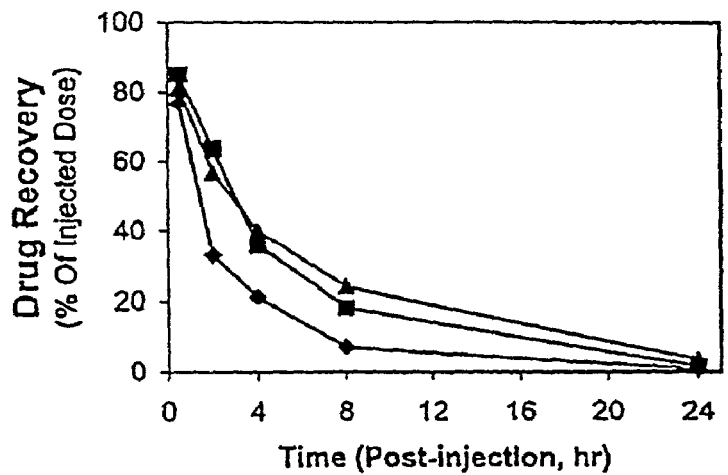

Administration of free topotecan as a single intravenous dose had minimal effect on survival in the L1210 model (see, FIG. 3A). At the highest dose of free topotecan, a median survival of 13 days (44% ILS) was observed. There was one long-term survivor (day 60) in this group. In contrast, a single i.v. administration of liposomal topotecan at either 5 or 10 mg/kg resulted in 100% survival at day 60 (see, FIG. 3B). Median survival for a 1 mg/kg dose was 13 days (44% ILS) and the survival curve was nearly identical to that of the free topotecan administered at 30 mg/kg-a 30-fold improvement in potency. At higher doses (30 mg/kg) of the liposomal topotecan, toxic deaths were observed. The MTD for liposomal topotecan was 20 mg/kg in BDF-1 mice after a single i.v. administration.

2. CT-26 Murine Colon Carcinoma. The murine CT-26 colon cell line is useful for drug screening since it readily grows as subcutaneous solid tumors or can be administered intravenously and used as a survival model. In addition, when the tumor cells are administered by intrasplenic injection, followed by splenectomy, the cells seed to the liver and give rise to an experimental metastases model that more closely resembles the clinical progression of colorectal cancer. The model has been used extensively and is described, for example, in detail elsewhere.

Figure 4A:
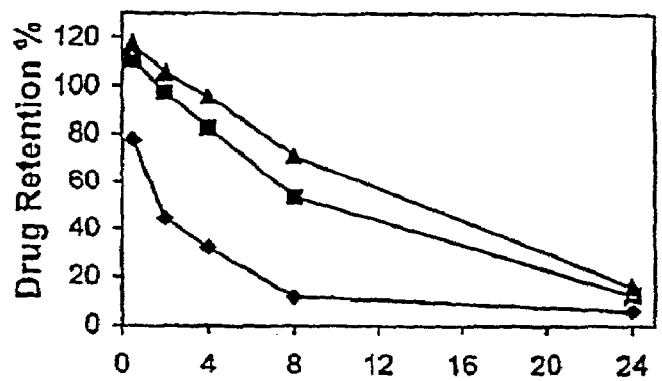
FIG. 4A-C shows the pharmacokinetic behavior of formulations of liposomal vinblastine as a function of drug: lipid ratio (plasma PK). Panel A shows drug retention versus time. Panel B shows lipid recovery versus time. Panel C shows drug release rates correlate with changes to drug clearance half-life from the plasma.
Figure 4B:
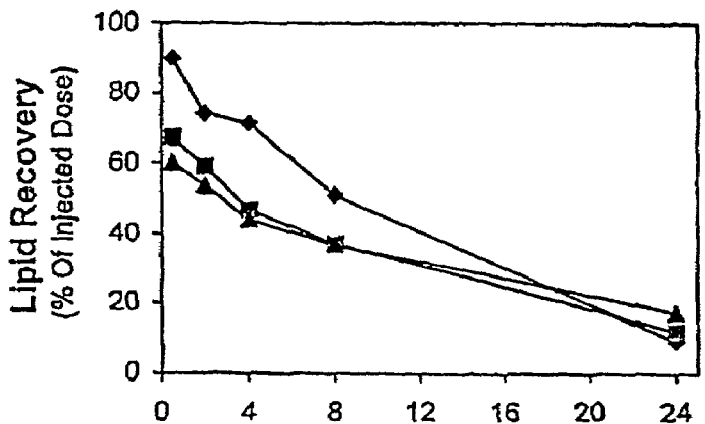
Figure 4C:
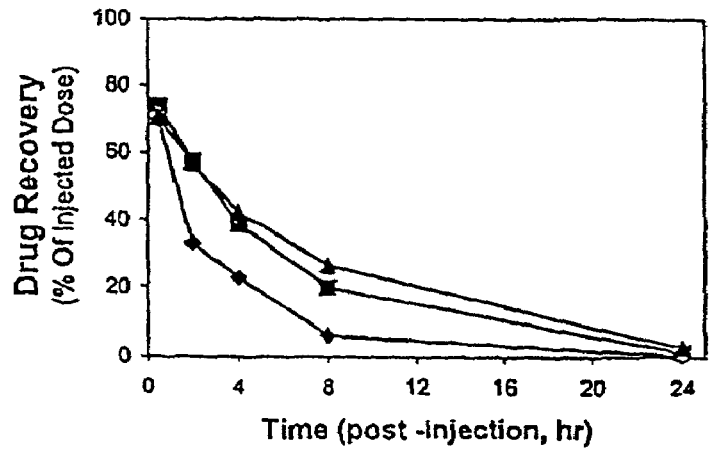

In the CT-26 model, administration of a single dose of topotecan had a modest impact on survival resulting in % ILS of 23-60% over the dose range 5-40 mg/kg (see, FIG. 4). Liposome encapsulated topotecan, however, was highly active at doses greater than 5 mg/kg, resulting in 100% survival (8/8) at day 90. At 10 mg/kg, 87.5% survival (7/8) was observed at day 90; however, the tumor burden in dead animal was very low suggesting that this animal may have died due to other factors, such as infection related to myelosuppression. A dose response was observed for liposomal topotecan, with the 2 mg/kg dose giving an % ILS of 54%. This was determined to be the MED and was comparable to the % ILS (58%) achieved using free topotecan at 40 mg/kg —a 20-fold increase in potency.

3. MX-1 Human Breast Carcinoma. Mx-1 is an experimental model of human breast cancer and has a reported doubling time of 3.9 days NCI); in this study, the median doubling time was consistently 3.6-3.7 days. The tumor cell line was derived from the primary tumor of a 29-year-old female with no previous history of chemotherapy and is provided by the DCTD (NCI) tumor repository as a tumor fragment that is serially passaged in nude mice. Histologically, MX-1 is a poorly differentiated mammary carcinoma with no evidence of gland formation or mucin production. MX-1 was one of 3 xenograft models (MX-1, LX-1, CX-1) that comprised the NCI in vivo tumor panel and prescreen (1976-1986) for evaluating novel chemotherapeutic agents (Plowman, et al., *Human tumor xenograft models in NCI drug development. In "Anticancer Drug Development Guide: Preclinical Screening, Clinical Trials, and Approval"* (B. Teicher, Ed.), Humana Press Inc., Totowa (1997)). Since then, MX-1 has been incorporated into a larger panel of breast tumor models (12 in total) to reflect a shift in NCI strategy from "compound-oriented" discovery to "disease-oriented" discovery.

Figure 5A:
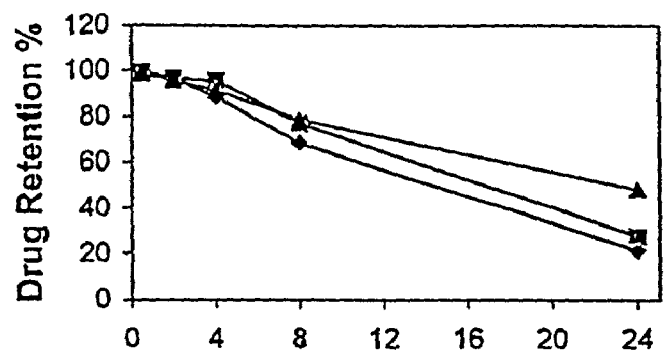
FIG. 5A-C shows the influence of lipid dose on PK behavior (blood PK). As illustrated therein, similar rates of drug release (A), lipid clearance (B) and drug clearance (C) are seen for a liposomal vinblastine formulation of drug: lipid ratio 0.3:1 over a lipid dose range of 16.6 mg/kg to 50 mg/kg.
Figure 5B:
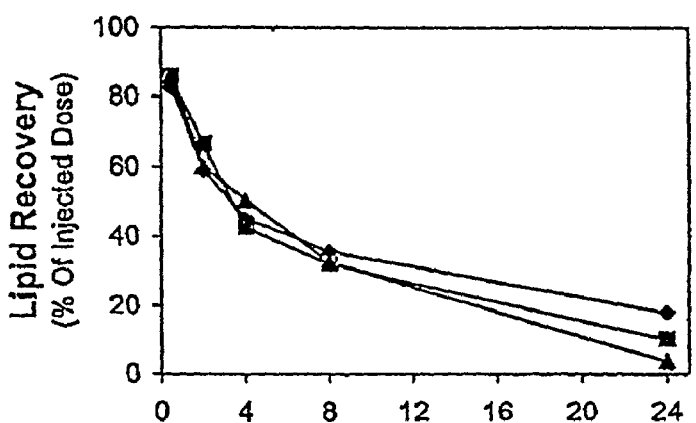
Figure 5C:
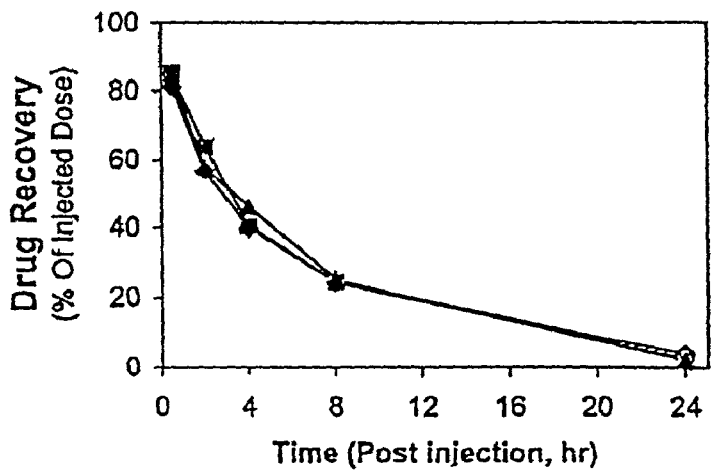

In staged (100-300 $mm^3$) MX-1 tumors, free topotecan exhibited dose-dependent inhibition of tumor growth (see, FIG. 5; Table I). At the highest dose (40 mg/kg), an optimal % T/C of 24% was obtained; while optimal % T/C values for 10 and 5 mg/kg were 66% and 78%, respectively. No drug-related deaths were observed and all animals gained weight throughout the study. Liposome encapsulation of topotecan had a marked impact on % T/C, with optimal % T/C values of 8%, −49% and −62% following a single administration of the drug at 2, 5 or 10 mg/kg, respectively. A negative % T/C value is indicative of tumor volume regression from the original staged tumor size (100-300 $mm^3$). According to NCI guidelines, an optimal % T/C <10% is considered significant activity, while values <42% are the minimum acceptable limits for advancing a drug further in development (Corbett, T. et al., In vivo *methods for screening and preclinical testing. In "Anticancer Drug Development Guide: Preclinical Screening, Clinical Trials, and Approval"* (B. Teicher, Ed.), Humana Press Inc., Totowa (1997)). Liposome encapsulation increased the toxicity of topotecan, reducing the MTD to 10 mg/kg from >40 mg/kg for free topotecan.

4. LX-1 Human Lung Carcinoma. LX-1 is an experimental model of human small cell lung cancer (SCLC). The tumor cell line was derived from the surgical explant of a metastatic lesion found in a 48 year old male and is provided by the DCTD (NCI) tumor repository as a tumor fragment that is serially passaged in nude mice. The LX-1 model was part of the NCI in vivo tumor panel from 1976-1986 (Plowman, J. et al, *Human tumor xenograft models in NCI drug development. In "Anticancer Drug Development Guide: Preclinical Screening, Clinical Trials, and Approval"* (B. Teicher, Ed.), Humana Press Inc., Totowa (1997)) and, although used less frequently now, remains a useful xenograft model for comparative activity studies between free and liposomal drugs because of its rapid growth rate.

Figure 6A:
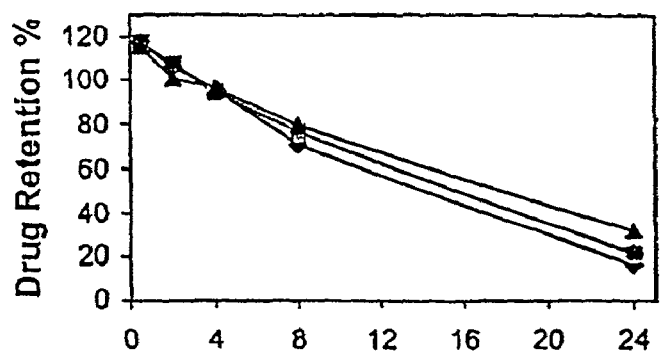
FIG. 6A-C shows the influence of lipid dose on PK behavior (plasma PK). As illustrated therein, similar rates of drug release (A), lipid clearance (B) and drug clearance (C) are seen for a liposomal vinblastine formulation of drug: lipid ratio 0.3:1 over a lipid dose range of 16.6 mg/kg to 50 mg/kg.
Figure 6B:
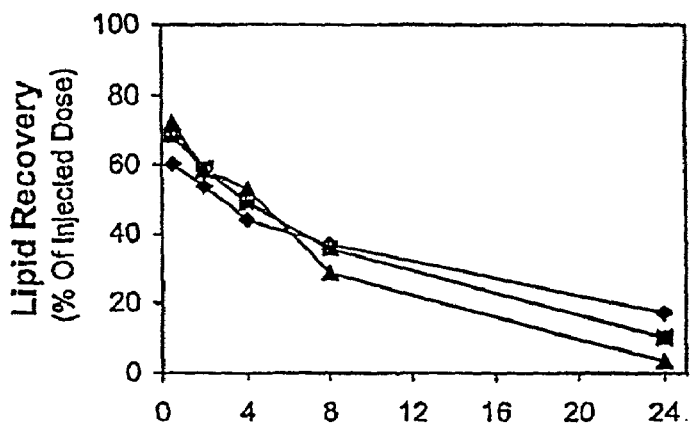
Figure 6C:
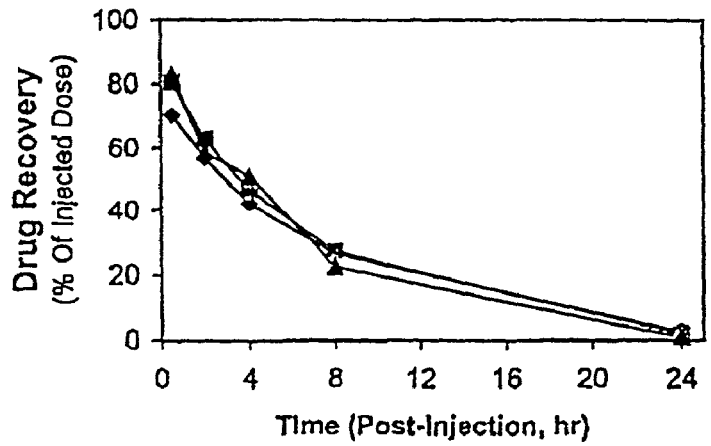

In general, the LX-1 model was less sensitive to the effects of topotecan than the MX-1 model, for both free and liposome-encapsulated drug (see, FIG. 6; Table I). Optimal % T/C values for free topotecan were 43%, 55% and 67% for doses of 30, 10 or 5 mg/kg, respectively. Anti-tumor activity was improved through encapsulation, resulting in % T/C values of 8%, 11% and 13% for doses of 30, 10, or 5 mg/kg, respectively. Interestingly, all of the liposomal topotecan doses exhibited similar activity. This was an early study and subsequent studies in other models (see, FIGS. 4-6) indicate dose response beginning at doses <5 mg/kg. This is consistent with the observation that camptothecin-class compounds (and presumably other antineoplastic agents) can exhibit "self-limiting" efficacy whereby, at doses above a critical threshold dose, no further activity benefits are observed (Thompson, *Biochim. Biophys. Acta* 1400:301-319 (1998)). This situation could conceivably occur if the drug has limited tumor cell access or if the drug is acting on, and destroying, the tumor vasculature (i.e., has anti-angiogenic activity). In both instances, a higher dose of drug would be expected to have negligible benefit.

As observed in the L1210 study, encapsulation of topotecan enhanced the toxicity of the drug and reduced the MTD. The MTD in tumor-bearing nude mice was 10 mg/kg (~16% weight loss). At 30 mg/kg, 4/6 drug-related toxic deaths were observed and maximum weight loss reached ~29% (27-34% range).

D. Efficacy Studies in Murine and Human Tumor Models: Multiple Dose Studies

Figure 7A:
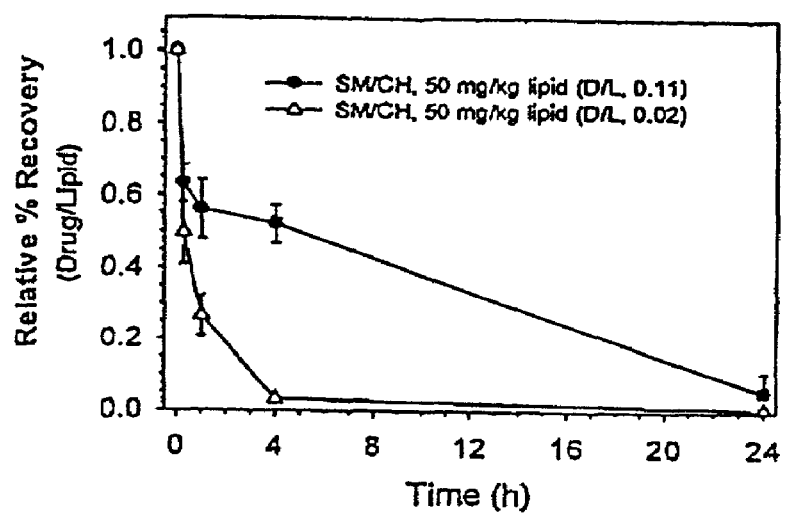
FIG. 7A-B shows the pharmacokinetic behavior of two formulations of liposomal topotecan of differing drug:lipid ratios. Panel A shows that when topotecan is loaded to a drug:lipid ratio of 0.11:1, a much slower drug release rate is seen resulting in a much longer plasma clearance rate compared to Panel B having a formulation of lower drug: lipid ratio of 0.02:1.
Figure 7B:
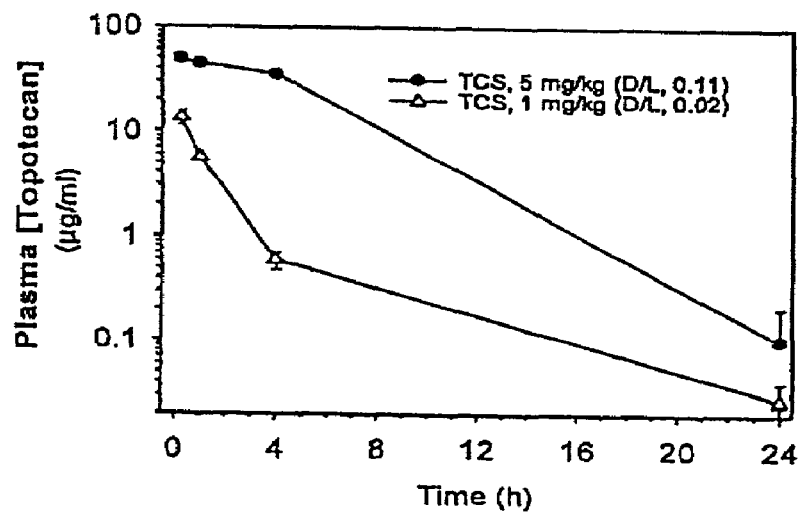

1. MX-1 Human Breast Carcinoma. To address the effectiveness of multiple administration and prolonged exposure of the tumors to drug, two multiple dose protocols were examined in MX-1 xenografts—q3dx4 and q7dx3 schedules. On the q4dx3 schedule, free topotecan exhibited moderate activity at 2.5 and 10 mg/kg/dose and minimal activity at 1.25 mg/kg/dose (see, FIG. 7; Table II). Optimal % T/C values for free topotecan on this dosing schedule were 55%, 30% and 27% for 1.25, 2.5 and 10 mg/kg/dose, respectively. For the encapsulated topotecan administered on the same dosing schedule, optimal % T/C values were −15%, −100%, −100%, and −100% for 0.5, 1.25, 2.5 and 5 mg/kg/dose, respectively. All regressed tumors were monitored for 60 days. At the end of this period, all animals treated with ≧1.25 mg/kg/dose of liposomal topotecan were considered tumor free.

On a q7dx3 dosing schedule, little activity was observed with the free topotecan, either a 5 or 10 mg/kg/dose (see, FIG. 8; Table II). At the same doses, liposomal topotecan induced complete regression of the staged tumors. However, on this dosing schedule, 10 mg/kg/dose was too toxic and this portion of the study was halted as 6/6 toxic deaths (or euthanasia's) were observed by day 24.

2. LX-1 Human Lung Carcinoma. Initial studies (single dose) in the LX-1 model indicated that free topotecan was inactive at evaluated doses <30 mg/kg and liposomal topotecan inhibited tumor growth, but did not induce regression. To improve this activity, a multiple (q7dx3) schedule was examined for both free and liposomal topotecan. In this instance, considerably greater activity was observed for free topotecan compared to the single dose study and optimal % T/C values of 5 and 40 were obtained for 30 and 10 mg/kg/dose, respectively. Liposomal topotecan also exhibited significantly improved activity, resulting in complete regression (with subsequent re-growth) at 5 mg/kg/dose. Optimal % T/C values for liposomal topotecan in this model and dosing schedule were −55, 3 and 16 for 5, 2.5, 1.25 mg/kg/day, respectively.

3. Therapeutic Index (TI) Comparisons. The therapeutic index of free and liposomal topotecan was assessed in 4 different tumor models on several different dosing schedules (see, Table 4). The assumptions and definitions used to generate these numbers are found in Table III. In some instances, a true MED or MTD was not observed and was therefore estimated mathematically based on dose response trends. For instance, an acute MTD of 40 mg/kg was observed for free topotecan administered as a single bolus injection, but the true MTD (based on weight loss) would likely be closer to 60 mg/kg if the drug was infused over 5-10 minutes. Also, complicating the analysis somewhat was the level of potency of the liposomal formulation. Significant anti-tumor activity was achieved at low drug doses and the MED had to be estimated in certain studies. In these instances, a notation was made in Table 4.

In general, the increase in therapeutic index for liposomal topotecan was relatively large for single dose administration (5, 10, 15 and 18-fold, depending on the model) and decreased with increasing dosing frequency. This is illustrated in Table 4, where the $TI_{TCS}/TI_{Free}$ ratio was 4.7-7.5 and 3.3 for q7dx3 and q3dx4 schedules, respectively. The decrease in the $TI_{TCS}/TI_{Free}$ ratio with more frequent dosing is consistent with preclinical and clinical studies indicating that the efficacy and toxicity of free topotecan is schedule-dependent.

TABLE 4

Relative Therapeutic Indices of Free and Liposomal Topotecan in Murine and Human Tumor Models.[a]

| Tumor Model | Route of Inoculation | Dosing Schedule | $TI_{Free}$ | $TI_{TCS}$ | $TI_{TCS}/TI_{Free}$ |
|---|---|---|---|---|---|
| L1210 (murine leukemia) | i.v. | single | 1.3 (2.0)[b] | 20 | 15.4 (10)[b] |
| CT-26 (murine colon) | i.s. | single | 1.0 (1.5)[b] | 5.0 | 5 (3.3)[b] |
| MX-1 (human breast) | s.c. | single | 1.4 (2.1)[b] | 25 | 17.9 (11.9)[b] |
|  |  | q3dx4 | 15 | 50[c] | 3.3 |
|  |  | q7dx3 | 2.0 | 15.0[c] | 7.5 |
| LX-1 (human lung) | s.c. | single | 1.3 (2.0)[b] | 13.3 | 10.2 (67)[b] |
|  |  | q7dx3 | 4.0 | 18.8 | 4.7 |

[a] based on data in Table II and III; formulas and definitions in Table IV.
[b] obtained using an acute MTD of 40 mg/kg; second value is based on an estimated MTD (body weight)
[c] a conservative estimate that may be ~2-fold greater; difficult to assess the MED due to high activity at low doses.

E. Discussion

Topotecan is an excellent candidate for liposome encapsulation. Briefly, topotecan is cell-cycle specific (S-phase) and activity is greatly enhanced with prolonged exposure, topotecan exhibits rapid plasma pharmacokinetics and the drug needs to be maintained below pH 6.0 to retain biological activity. This is an ideal scenario for using a relatively non-leaky liposome formulation (such as SM:CH, 55:45) that has an acidic aqueous core. The required acidic interior can be produced, for example, by pH-loading or ionophore loading methodology. Here, it has been demonstrated that encapsulation of topotecan in SM/CH liposomes by the Mg-A23187 method results in dramatic enhancements in anti-tumor efficacy. Modest enhancement of toxicity was also observed for liposomal topotecan, but this was largely offset by substantial dose reductions that achieved comparable and, in most instances, superior efficacy relative to the free drug.

Therapeutic index (TI) is a useful parameter of drug activity, as it is measure of the ratio of toxicity (MTD) to biological activity (user defined endpoint, i.e., MED, $ED_{50}$, or $ED_{80}$). In general, the lower the TI, the greater the risk of toxicity since the dose of drug required to elicit a biological effect approaches the MTD. Therapeutic index is particularly useful for the evaluation of liposomal drugs since the relative change in TI can be used to define the benefit (or lack thereof) of encapsulation. As demonstrated herein, the TI improved from 3-18 fold depending on the model and dose schedule used. Therefore, the improvement in biological activity observed following liposome encapsulation of topotecan more than compensates for any increases in toxicity.

Without intending to be bound by any theory, it is thought that the significant improvements in anti-tumor activity and the increased toxicity of the liposomal form of the drug result from improved pharmacokinetics and the maintenance of the drug in the active lactone form. In these studies, 84% of topotecan was present in plasma as the lactone species after 24 h compared to 48% lactone for free topotecan after only 5 minutes. Moreover, when the same dose (10 mg/kg) of free and liposomal topotecan was administered intravenously in mice, the concentration of lactone was ~40-fold higher at times <1 h. At 24 h, the lactone plasma concentration for liposomal drug was 5.4 μg/ml compared to 1.5 μg/ml at 5 minutes for free drug—still 3.5-fold greater than the peak lactone concentration for free topotecan.

TABLE I

Summary of Single Dose Anti-Tumor Activity and Toxicity Parameters

| Model | | Dose | Anti-Tumor Activity | | | | | Toxicity | |
|---|---|---|---|---|---|---|---|---|---|
| | | | % T/C[a] | T-C[b] | % ILS[c] | LCK[d] | TF[e] | DRD[f] | MWL[g] |
| L1210 | Free | 5 | | | 11 | | 0/8 | 0/8 | + |
| (i.v.) | Free | 10 | | | 22 | | 0/8 | 0/8 | + |
| NCTEF-005 | Free | 20 | | | 33 | | 0/8 | 0/8 | + |
| | Free | 30 | | | 44 | | 0/8 | 0/8 | + |
| | Free | 40 | | | 55 | | 0/8 | 0/8 | + |
| | TCS | 1 | | | 44 | | 0/8 | 0/8 | + |
| | TCS | 5 | | | ** | | 8/8 | 0/8 | + |
| | TCS | 10 | | | ** | | 8/8 | 0/8 | −9.7 |
| | TCS | 20 | | | ** | | 7/7 | 1/8 | −14.8 |
| | TCS | 30 | | | ** | | 3/3 | 5/8 | −23.4 |
| CT-26 | Free | 5 | | | 31 | | 0/8 | 0/8 | + |
| (i.s.) | Free | 10 | | | 23 | | 0/8 | 0/8 | + |
| NCTEF-005 | Free | 40 | | | 58 | | 1/8 | 0/8 | −0.4 |
| | TCS | 2 | | | 54 | | 0/8 | 0/8 | + |
| | TCS | 5 | | | ** | | 8/8 | 0/8 | −6.8 |
| | TCS | 10 | | | ** | | 7/8 | 0/8 | −19.1 |
| MX-1 | Free | 5 | 78 | 0.2 | 0 | 0.02 | 0/6 | 0/6 | + |
| (s.c.) | Free | 10 | 66 | 1.4 | 13 | 0.12 | 0/6 | 0/6 | + |
| NCTEF-004 | Free | 40 | 24 | 4.2 | 35 | 0.35 | 0/6 | 0/6 | + |
| | TCS | 2 | 8 | 7.4 | 65 | 0.62 | 0/6 | 0/6 | + |
| | TCS | 5 | −49 | 10.2 | 74 | 0.85 | 0/6 | 0/6 | −0.4 |
| | TCS | 10 | −62 | 14.2 | 83 | 1.19 | 1/6 | 0/6 | −18.3 |
| LX-1 | Free | 5 | 67 | 1.4 | 0 | 0.13 | 0/6 | 0/6 | + |
| (s.c.) | Free | 10 | 55 | 1.9 | 0 | 0.18 | 0/6 | 0/6 | + |
| NCTEF-003 | Free | 30 | 43 | 2.9 | 7 | 0.27 | 0/6 | 0/6 | −1.3 |
| | TCS | 5 | 13 | 7.9 | 30 | 0.74 | 0/6 | 0/6 | −1.7 |
| | TCS | 10 | 11 | 8.7 | 22 | 0.82 | 0/6 | 0/6 | −15.6 |
| | TCS | 30 | 8 | 9.9 | 22 | 0.93 | 0/6 | 4/6 | −29.0 |

[a] optimal % T/C following final treatment. Negative value indicates tumor regression.
[b] tumor growth delay (difference in time for treated and control tumors to reach 500 mm$^3$).
[c] increase in lifespan relative to untreated animals (expressed as %).
[d] log cell kill (gross).
[e] tumor free animals at the end of study (i.e. no visible tumors or long term survivors).
[f] drug related deaths.
[g] maximum mean weight loss per treatment group.
[h] positive weight change (i.e. at no time did weight decrease below pre-treatment weight).
** long term survivors

TABLE II

Summary of Multiple Dose Anti-Tumor Activity and Toxicity Parameters

| Model | | Dose | Anti-Tumor Activity | | | | | Toxicity | |
|---|---|---|---|---|---|---|---|---|---|
| | | | % T/C[a] | T-C[b] | % ILS[c] | LCK[d] | TF[e] | DRD[f] | MWL[g] |
| MX-1 | Free | 1.25 | 55 | 2.0 | 20 | 0.17 | 0/6 | 0/6 | +[h] |
| (q3dx4) | Free | 2.5 | 30 | 5.0 | 55 | 0.42 | 0/6 | 0/6 | + |
| NCTEF-006 | Free | 10 | 27 | 2.5 | 52 | 0.21 | 1/6 | 0/6 | + |
| | TCS | 0.5 | −15 | 23.5 | 157 | 1.96 | 1.6 | 0/6 | −0.3 |
| | TCS | 1.25 | −100 | ** | ** | | 6/6 | 0/6 | −1.0 |
| | TCS | 2.5 | −100 | ** | ** | | 6/6 | 0/6 | −11.5 |
| | TCS | 5 | −100 | ** | ** | | 6/6 | 0/6 | −20.0 |
| MX-1 | Free | 5 | 58 | 1.8 | 27 | 0.15 | 0/6 | 0/6 | + |
| (q7dx3) | Free | 10 | 61 | 2.0 | ND[i] | | 0/6 | 0/6 | −0.8 |
| NCTEF-009 | TCS | 5 | −100 | ** | ** | | 6/6 | 0/6 | −7.6 |
| | TCS | 10 | −100 | ND[i] | ND[i] | | 6/6 | 6/6 | −29.0 |

TABLE II-continued

Summary of Multiple Dose Anti-Tumor Activity and Toxicity Parameters

| Model | | Dose | % T/C[a] | T-C[b] | % ILS[c] | LCK[d] | TF[e] | DRD[f] | MWL[g] |
|---|---|---|---|---|---|---|---|---|---|
| LX-1 | Free | 10 | 40 | 2.0 | 21 | 0.14 | 0/6 | 0/6 | −6.2 |
| (q7dx3) | Free | 30 | 5 | 20.9 | 58 | 1.53 | 0/6 | 0/6 | −8.8 |
| NCTEF-007 | TCS | 1.25 | 16 | 10.8 | 54 | 0.79 | 0/6 | 0/6 | −7.7 |
| | TCS | 2.5 | 3 | 23.2 | 79 | 1.70 | 0/6 | 0/6 | −7.3 |
| | TCS | 5 | −55 | 30.2 | 100 | 2.22 | 0/6 | 0/6 | −10.5 |
| LX-1 | Free | 10 | 28 | 4.4 | 41 | | 0/6 | 0/6 | −3.6 |
| (q7dx3) | Free | 30 | 9 | 25 | 72 | | 0/6 | 2/6 | −16.4 |
| NCTEF-011 | TCS | 7.5 | ND[i] | ND[i] | ND[i] | | 0/6 | 6/6 | >−30 |
| | TCS | 0.75 | 27 | 11.2 | 50 | | 0/6 | 0/6 | −1.3 |

[a]optimal % T/C following final treatment. Negative value indicates tumor regression.
[b]tumor growth delay (difference in time for treated and control tumors to reach 500 mm3).
[c]increase in lifespan relative to untreated animals (expressed as %).
[d]log cell kill (gross).
[e]tumor free animals at the end of study (i.e. no visible tumors or long term survivors).
[f]drug related deaths.
[g]maximum mean weight loss per treatment group.
[h]positive weight change (i.e. at no time did weight decrease below pre-treatment weight).
[i]not determined; toxic deaths in the liposome-encapsulated group.
***"cures"; no visible tumors by day 60.

TABLE III

Definitions and Formulas for Toxicity and Anti-Tumor Activity Parameters

| | |
|---|---|
| DRD | Drug-related death. A death was considered drug-related if the animal died or was euthanized within 15 days following the final treatment with drug AND its tumor weight was less than the lethal burden on control mice, or its weight loss was greater than 20% that of the control animals. |
| $GI_{50}$ | The concentration of drug that causes 50% growth inhibition in a population of cells in vitro. The NCI renamed the $IC_{50}$ parameter to emphasize the correction for cell count at time zero. Therefore, the formula is: $GI_{50} = (T - T_o)/(C - T_o) \times 100 = 50$ T and $T_o$ are the optical densities at 48 and 0 h, respectively; C is the control (cell count) optical density at 0 h. |
| % ILS | Increase in lifespan (in percent). For survival models this is calculated using the median survival times for the treated ($T_{treat}$) and control ($T_{cont}$) animals, according to: $(T_{treat} - T_{cont})/T_{cont} \times 100$ For the solid tumor models, the time for tumors to reach 2000 mm³ (~10% of body weight) was used as an ethical cutoff instead of median survival. |
| LCK | Log cell kill (gross). This parameter estimates the number of $log_{10}$ units of cells killed at the end of treatment, according to the formula: (T − C) × 0.301/median doubling time Net log cell kill can be calculated by subtracting the duration of treatment from the tumor growth delay (T − C) parameter as follows: [(T − C) − duration of treatment] × 0.301/median doubling time A log cell kill of 0 indicates that the cell population at the end of treatment is the same as it was at the onset of treatment. However, a log cell kill of 4, for example, indicates a 99.99% reduction in the initial cell population. |
| MBWL | Maximum body weight loss (in percent). The animals are weighed prior to the first administration of the drug (Wi) and on various days during the study (Wd). The percent change in body weight is calculated by: $MBWL = (W_d - W_i)/W_i \times 100$ |
| MED | Minimum effective dose. For these studies we have defined the MED as the lowest dose achieving an optimal % T/C ≤ 40 (for solid tumor models) or a % ILS of 40–60% (for survival models). |
| MTD | Maximum tolerated dose. Dose of drug that results in a MBWL of ≤20%. |
| % T/C | Optimal ratio of treated vs control tumors obtained following the first course of treatment. These values are obtained by subtracting the median tumor weight on the first day of treatments ($T_i$ or $C_1$) from the tumor weights on each observation day according to the following formula: % T/C = ($\Delta$ T/$\Delta$ C) × 100, where $\Delta$ T > 0, or % T/C = ($\Delta$ T/$T_1$) × 100, where $\Delta$ T < 0 According to NCI activity criteria, the following scoring system applies (Plowman, et al., Human tumor xenograft models in NCI drug development. In "Anticancer Drug Development Guide: Preclinical Screening, Clinical Trials, and Approval" (B. Teicher, Ed.), Humana Press Inc., Totowa (1997)[22]: 0 = inactive, % T/C > 40 1 = tumor inhibition, % T/C range 1–40 2 = tumor stasis, % T/C range 0 to −40 3 = tumor regression, % T/C range −50 to −100 4 = % T/C range −50 to −100 and > 30% tumor-free mice |
| TGD | Tumor growth delay (also represented as T − C). This parameter expresses the difference in time (in days) for treated and control tumors to attain an arbitrary size (typically 500 or 1000 mm³). |
| TI | Therapeutic index. Therapeutic index is the ratio of a toxicity parameter (i.e. $LD_{50}$, $LD_{10}$, MTD) and a biological activity parameter (i.e. $ED_{50}$-the dose that causes a defined biological response in 50% of the treatment group). In general, TI describes the margin of safety for a drug. For animal model studies this is traditionally described by the formula: $TI = LD_{50}/ED_{50}$ However, since it is no longer ethically permissible to perform $LD_{50}$ studies, we have defined therapeutic index for these studies as: TI = MTD/MED |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A liposomal formulation, said liposomal formulation comprising a liposome having vinorelbine in solution and precipitated vinorelbine, wherein the precipitated vinorelbine in said liposome is at least 50% of the total vinorelbine, wherein said liposome comprises sphingomyelin and cholesterol at a ratio in the range of about 75/25 mol %/mol % sphingomyelinl/cholesterol to about 30/50 mol %/mol % sphingomyelinl/cholesterol, and wherein the ratio of said vinorelbine to lipid is 0.2-0.3:1 (w/w).

2. The liposomal formulation of claim 1, wherein said liposome comprises sphingomyelin and cholesterol in a 55:45 molar ratio.

3. The liposomal formulation of claim 1, wherein said liposome comprises sphingomyelin and cholesterol in a 50:50 molar ratio.

4. The liposomal formulation of claim 1, wherein the ratio of said vinorelbine to said lipid is about 0.3:1 (w/w).

5. A liposomal formulation, said liposomal formulation comprising a liposome having vinorelbine in solution and precipitated vinorelbine, wherein the precipitated vinorelbine in said liposome is at least 50% of the total vinorelbine, wherein said liposome comprises sphingomyelin and cholesterol at a ratio of about 55/45 mol %/mol % sphingomyelin/cholesterol, and wherein the ratio of said vinorelbine to lipid is about 0.3:1 (w/w).

* * * * *